United States Patent
Takahashi et al.

(10) Patent No.: US 7,948,618 B2
(45) Date of Patent: May 24, 2011

(54) DEFECT INSPECTION METHOD AND APPARATUS WITH A THRESHOLD VALUE DETERMINATION

(75) Inventors: Naohiro Takahashi, Kawasaki (JP); Tamihide Yasumoto, Kawasaki (JP); Tadamasa Noguchi, Kawasaki (JP)

(73) Assignee: Fujitsu Semiconductor Limited, Yokohama (JP)

( * ) Notice: Subject to any disclaimer, the term of this patent is extended or adjusted under 35 U.S.C. 154(b) by 0 days.

(21) Appl. No.: 11/580,870

(22) Filed: Oct. 16, 2006

(65) Prior Publication Data

US 2007/0285653 A1 Dec. 13, 2007

(30) Foreign Application Priority Data

Jun. 13, 2006 (JP) ................... 2006-163776

(51) Int. Cl.
*G01N 21/88* (2006.01)
(52) U.S. Cl. ............ 356/237.2; 356/72
(58) Field of Classification Search ..... 356/237.2–237.5
See application file for complete search history.

(56) References Cited

U.S. PATENT DOCUMENTS

| | | | | |
|---|---|---|---|---|
| 7,355,709 B1* | 4/2008 | Bevis et al. | ............... | 356/390 |
| 7,851,753 B2* | 12/2010 | Uto et al. | ............... | 250/310 |
| 2001/0019411 A1* | 9/2001 | Nara et al. | ............... | 356/394 |
| 2002/0044278 A1* | 4/2002 | Le | ............... | 356/237.3 |
| 2003/0038932 A1* | 2/2003 | Wienecke et al. | ........ | 356/237.2 |
| 2004/0158409 A1* | 8/2004 | Teshima et al. | ............... | 702/22 |
| 2005/0194535 A1* | 9/2005 | Noji et al. | ............... | 250/311 |
| 2006/0082763 A1* | 4/2006 | Teh et al. | ............... | 356/72 |
| 2006/0238753 A1* | 10/2006 | Tsuji et al. | ............... | 356/237.2 |

FOREIGN PATENT DOCUMENTS

| | | |
|---|---|---|
| JP | 2002-267625 A | 9/2002 |
| JP | 2002-303587 A | 10/2002 |

* cited by examiner

*Primary Examiner* — Gregory J Toatley
*Assistant Examiner* — Rebecca C Slomski
(74) *Attorney, Agent, or Firm* — Westerman, Hattori, Daniels & Adrian, LLP

(57) ABSTRACT

Scattered light from the surface of a sample subjected to the same process as a process for an inspection object is observed, a defect is detected from an intensity of scattered light, and a position of the detected defect and an intensity of scattered light caused by the detected defect are acquired. Defects detected are classified into a group detectable by observing secondary electrons emitted when an electron beam is applied to the surface of the sample and a group not detectable. A decision threshold value of a scattered light intensity for extracting defects to be counted is determined, in accordance with a result of classification by the above steps and the intensity of scattered light caused by the detected defect.

3 Claims, 6 Drawing Sheets

FIG.2

| PRODUCT TYPE | STEP | CHIP LAYOUT | LASER IRRADIATION CONDITION | DECISION THRESHOLD |
|---|---|---|---|---|
| A | a | L1 | Ir1 | Ith1 |
| A | b | L1 | Ir2 | Ith2 |
| A | c | L1 | Ir3 | Ith3 |
| A | d | L1 | Ir4 | Ith4 |
| | ⋮ | | | |
| B | a | L2 | Ir1 | Ith1 |
| B | b | L2 | Ir2 | Ith2 |
| B | c | L2 | Ir3 | Ith3 |
| B | d | L2 | Ir4 | Ith4 |
| | ⋮ | | | |
| C | a | L1 | Ir1 | Ith1 |
| C | b | L1 | Ir2 | Ith2 |
| C | c | L1 | Ir3 | Ith3 |
| C | d | L1 | Ir4 | Ith4 |
| | ⋮ | | | |

DEFECT INSPECTION METHOD AND APPARATUS WITH A THRESHOLD VALUE DETERMINATION

CROSS REFERENCE TO RELATED APPLICATION

This application is based on and claims priority of Japanese Patent Application No. 2006-163776 filed on Jun. 13, 2006, the entire contents of which are incorporated herein by reference.

BACKGROUND OF THE INVENTION

A) Field of the Invention

The present invention relates to a defect inspection method and apparatus for semiconductor wafers subjected to various processes.

B) Description of the Related Art

JP-A-2002-303587 discloses a surface inspection method by which a surface of a wiring pattern on an uppermost layer is scanned with a laser beam and an intensity of reflected or scattered light is compared with a threshold value to inspect defects such as attachment of foreign matters.

JP-A-2002-267625 discloses a defect inspection method by which image data of two different chips on a semiconductor wafer is compared to extract defects based on a difference between image data. This method judges as a defect a region having a luminance difference between image data of two chips equal to or larger than a threshold value.

SUMMARY OF THE INVENTION

The methods disclosed in JP-A-2002-303587 and JP-A-2002-267625 detect a defect from a comparison result between a threshold value and an intensity of light scattered from the surface of a semiconductor wafer or a luminance difference of image data. If the threshold value is set too high, a defect otherwise to be detected may be overlooked. If the threshold value is set too low, a region without defect may be detected as a defect. The threshold value has conventionally been set empirically from inspection results of a plurality of standard samples prepared beforehand.

The threshold value is required to be set for each of product types and each of processes under inspection. Therefore, each time a new product type is added to a manufacture line, it becomes necessary to form a plurality of samples and set a threshold vale.

It is an object of the present invention to provide a defect inspection method capable of determining a proper threshold value to be used for counting the number of defects. It is another object of the present invention to provide a defect inspection method and apparatus capable of determining a threshold value relatively easily even if a new product type is added to a manufacture line.

According to one aspect of the present invention, there is provided a defect inspection method comprising steps of:

(a) observing scattered light from a surface of a sample subjected to a same process as a process for an inspection object, detecting a defect from an intensity of scatted light, and acquiring a position of the detected defect and an intensity of scattered light caused by the detected defect;

(b) classifying defects detected at the step (a) into a group detectable by observing secondary electrons emitted when an electron beam is applied to the surface of the sample and a group not detectable; and (c) determining a decision threshold value of a scattered light intensity for extracting defects to be counted, in accordance with a result of classification by the step (b) and the intensity of scattered light caused by the detected defect.

According to another aspect of the present invention, there is provided a defect inspection method of applying a laser beam to a surface of a wafer, detecting a defect in accordance with an intensity distribution of scattered light from the surface, comparing an intensity of scattered light caused by the detected defect with a decision threshold value and counting defects in accordance with a comparison result, the defect inspection method comprising steps of:

(a) in response to a defect inspection request about a wafer of a first product type subjected to processing by a first process, judging whether the decision threshold value associated with the first process of the first product type is already registered; and (b) if it is judged at the step (a) that the decision threshold value is already registered, counting defects in accordance with the already registered decision threshold value, whereas if it is judged that the decision threshold value is not already registered, determining a new decision threshold value and counting defects and registering the newly determined decision threshold value in correspondence with the first process of the first product type.

According to still another aspect of the present invention, there is provided a defect inspection apparatus of applying a laser beam to a surface of a wafer, detecting a defect in accordance with an intensity distribution of scattered light from the surface, comparing an intensity of scattered light caused by the detected defect with a decision threshold value and counting defects in accordance with a comparison result, the defect inspection apparatus comprising:

a decision threshold value register for registering the decision threshold value for each product type and each process; and a controller, wherein the controller executes steps of:

(a) in response to a defect inspection request about a wafer of a first product type subjected to processing by a first process, judging whether the decision threshold value associated with the first process of the first product type is already registered; and (b) if it is judged at the step (a) that the decision threshold value is already registered, counting defects in accordance with the already registered decision threshold value, whereas if it is judged that the decision threshold value is not already registered, notifying an operator of an indication that the decision threshold value is still not registered.

Detected defects are classified into the group detectable by observing secondary electrons emitted when an electron beam is applied to the surface of a sample and the group undetectable, and the decision threshold value is determined from the classification result. It is therefore possible to prevent detection of inner layer defects not directly related to the process to be inspected. A judgment precision of whether the process is normal or abnormal can be increased.

If the decision threshold value for the product type to which an inspection request was issued is not registered, inspection is performed by using the decision threshold value for the same process of a different product type. It is therefore unnecessary to calculate the decision threshold value each time a new product type is added to a manufacture line.

BRIEF DESCRIPTION OF THE DRAWINGS

FIG. 2 is a table showing types of inspection recipes.

DESCRIPTION OF THE PREFERRED EMBODIMENTS

Figure 1A:
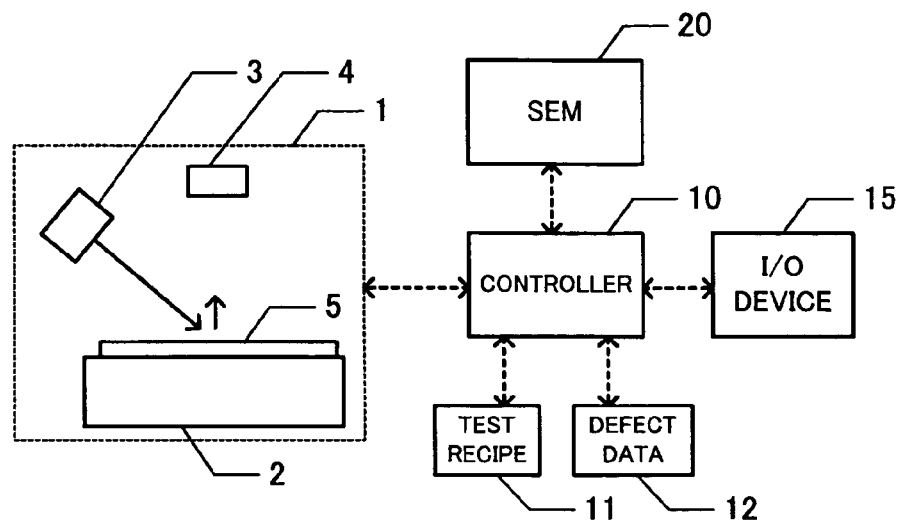
FIG. 1A is a block diagram of a defect inspection apparatus according to an embodiment.

FIG. 1A is a block diagram of a defect inspection apparatus of the embodiment. A measurement unit 1 includes a stage 2, a laser source 3 and an optical detector 4. An inspection object, for example, a semiconductor wafer 5 subjected to a process, is placed on the stage 2. A laser beam emitted from the laser source 3 is applied obliquely to the surface of the semiconductor wafer 5. Light scattered from the surface of the semiconductor wafer 5 is detected with the optical detector 4. By two-dimensionally scanning the laser beam emitted from the laser source 3 on the surface of the semiconductor wafer 5, it becomes possible to obtain an intensity distribution of scattered light on the surface of the semiconductor wafer 5.

An intensity of scattered light detected with the optical detector 4 is input to a controller 10. The controller 10 generates an intensity distribution (two-dimensional image data) of scattered light by using scanning data on the laser beam emitted from the laser source 3 and the intensity of scattered light supplied from the optical detector 4. Instead of the optical detector 4, a two-dimensional imaging apparatus, e.g., a CCD camera or the like, may be used to obtain two-dimensional image data by uniformly illuminating an inspection object area of the surface of the semiconductor wafer 5.

A plurality of chips are disposed regularly, for example, in a matrix shape, on the surface of the semiconductor wafer 5. A pattern formed in one chip, e.g., an element isolation region pattern, a gate electrode pattern, a wiring pattern or the like, is congruent to a corresponding pattern formed in another chip.

An I/O device 15 supplies the controller 10 with inspection information, and an inspection result is displayed on the I/O device 15. For example, the I/O device 15 is constituted of a keyboard, a mouse, a pattern recognition apparatus, a display device, a printer or the like. An operator inputs a product type of a semiconductor wafer to be inspected, a serial number affixed to the semiconductor wafer and the like from a keyboard, a mouse or the like. A product type, a serial number and the like marked on the surface of a semiconductor wafer may be automatically detected with a pattern recognition apparatus.

Inspection recipes (test recipes) are registered in an inspection recipe register 11.

FIG. 2 shows examples of inspection recipes. Chip layout information, laser irradiation conditions, and decision (judgment) threshold values are registered for each of product types and for each of manufacture processes. The chip layout information includes position and size information on chips disposed on the surface of a semiconductor wafer. The laser irradiation condition includes a power of an inspection laser beam to be emitted from the laser source 3 shown in FIG. 1A, an incidence angle and an azimuth angle of a laser beam relative to the surface of the semiconductor wafer 5. The decision threshold value is information to be used as a criterion of extracting defects to be counted from a measured scattered light intensity distribution.

For example, a chip layout of a semiconductor wafer for a product type A is L1. A laser beam is irradiated to the semiconductor wafer under the laser irradiation condition Ir1 for a process a to conduct defect inspection. A decision threshold value to be used for comparing with the number of counted defects is Ith1. The chip layout is generally the same even if processes are changed, if the product type is the same.

For example, the process a corresponds to a chemical mechanical polishing (CMP) process to be executed when an element isolation insulating film is formed by a shallow trench isolation method. A process b corresponds to a process of forming a gate electrode by pattering a polysilicon film. A process c corresponds to a CMP process for a tungsten film to be used for forming a tungsten plug filling a via hole formed through a first layer interlayer insulating film. A process d corresponds to a CMP process for a Cu plated film to be used for forming an upper wiring layer by a damascene method.

The controller 10 controls the laser source 3 in accordance with an inspection recipe registered in the inspection recipe register 11. An intensity of scattered light detected with the optical detector 4 is input to the controller 10. The controller 10 generates an intensity distribution of the scattered light from the scan position of a laser beam and an intensity of scattered light supplied from the optical detector 4.

Figure 1B:
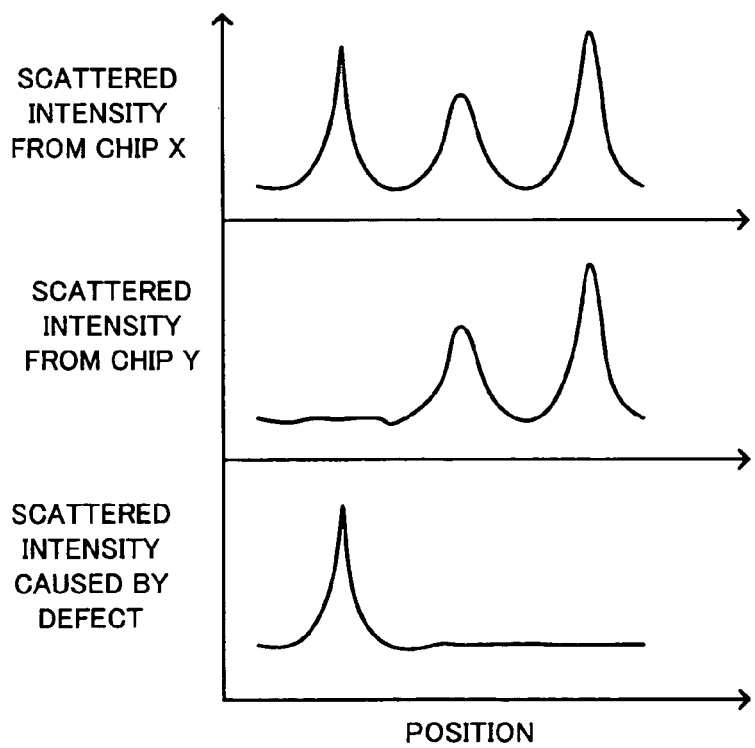
FIG. 1B is a graph showing examples of intensity distributions of scattered light from chip surfaces and an intensity distribution (differential image) of scattered light caused by a defect.

First and second rows of FIG. 1B show examples of intensity distributions of scattered light from the surfaces of chips X and Y. FIG. 1B shows simply a one-dimensional intensity distribution although the intensity distribution of scattered light is actually two-dimensional. The intensity of scattered light changes with a reflectivity difference between materials exposed on the chip surface, steps formed on the chip surface and the like.

The controller 10 calculates a difference between intensity distributions of scattered light from the surfaces of the chips X and Y. This intensity distribution difference is called a "differential image".

A third row in FIG. 1 shows an example of the differential image. The third row simply shows a one-dimensional differential image although a difference image is actually a two-dimensional image. Since congruent patterns are formed on the surfaces of the chips A and B, the intensity distributions of scattered light of both the chips are ideally coincident. However, if there is a defect such as foreign matter attachment and a lost pattern, there is a large difference in the intensity of scattered light from the defect. Namely, the differential image shown in the third row in FIG. 1 is considered as an intensity distribution of scattered light caused by the defect.

If the intensity of scattered light is uniform under the condition that there is no defect, e.g., if inspection is conducted after a process of forming a thin film on a uniform surface still not formed with a pattern, then it is not necessary to obtain a differential image, but it is possible to detect a defect from scattered light only from one chip.

The controller 10 calculates from the differential image the position (coordinate values) of a defect and an intensity of scattered light caused by the defect, and stores this information in a defect data storage 12.

The defect detected from the differential image is observed with a scanning electron microscope (SEM) 20. SEM can obtain two-dimensional image data by scanning the surface of a semiconductor wafer with an electron beam and observing secondary electrons emitted from the wafer surface. An operator may manipulate SEM 20 to observe each defect on the semiconductor wafer 5, or alternatively the controller 10 may supply defect position data to SEM 20 to allow SEM 20 to automatically acquire the image at that position.

Next, with reference to FIGS. 3 to 6F, description will be made on a defect inspection method using the defect inspection apparatus shown in FIG. 1A.

Figure 3:
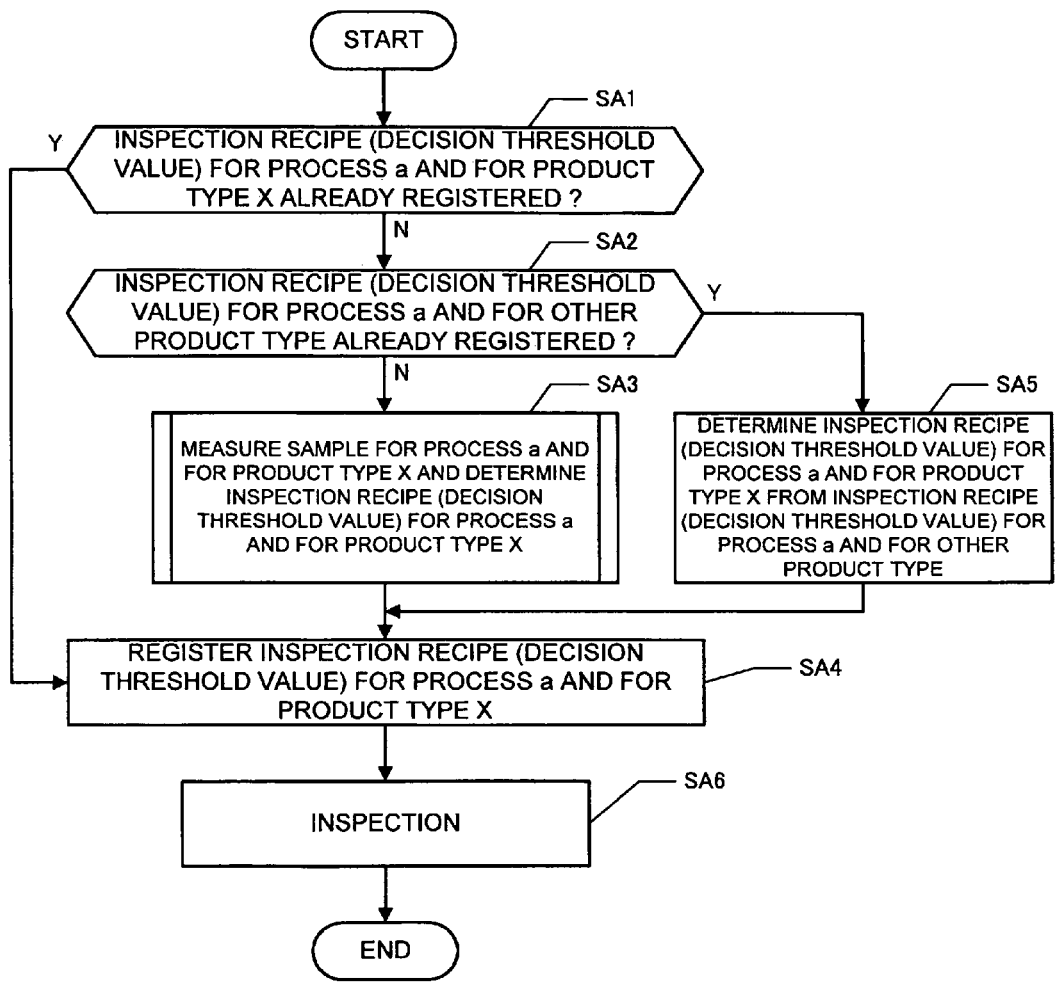
FIG. 3 is a flow chart illustrating a defect inspection method according to an embodiment.

FIG. 3 is a flow chart illustrating the defect inspection method. Upon an inspection request about a semiconductor wafer of a product type X subjected to a process a, it is judged at step SA1 whether there exists an inspection recipe for the product type X and for the process a. Of the inspection recipe, the chip layout information is already decided at the design stage. The laser irradiation condition suitable for inspection is known beforehand from the surface condition of the semiconductor wafer. It is therefore possible to use, as the laser irradiation condition for inspection for the process a, the laser irradiation condition suitable for inspection of a semiconductor wafer having a similar surface condition to that of the semiconductor wafer subjected to the process a. Accordingly, in practice, judgment at Step SA1 for existence of the inspection recipe is equivalent to judgment of whether a decision threshold value is registered or not. If the inspection recipe (decision threshold value) is already registered, inspection can be conducted at Step SA6, whereas if the inspection recipe (decision threshold value) is not registered, Step SA2 is executed.

At Step SA2, it is checked whether an inspection recipe (decision threshold value) for the process a and for another product type is registered or not. If the process to be inspected is the same, the surface condition of the semiconductor wafer and the internal lamination structure are the same even if the product type is different. Therefore, the inspection recipe (decision threshold value) for the process a and for the other product type can be used directly as the inspection recipe for the process a and for the product type X.

As a result, if the inspection recipe (decision threshold value) for the process a and for the other product type is already registered, at Step SA5 the inspection recipe (decision threshold value) for the process a and for the product type X is determined from the already registered inspection recipe (decision threshold value). The determined inspection recipe (decision threshold value) is registered at Step SA4 in the inspection recipe register 11, and the inspection is performed at Step SA6.

If it is judged at Step SA2 that the inspection recipe (decision threshold value) for the process a is not still registered, an indication that the inspection recipe (decision threshold value) is still not registered is notified to an operator via the I/O unit 15. The operator executes Step SA3 to create a new inspection recipe (decision threshold value). The newly created inspection recipe is registered in the inspection recipe register 11 at Step SA4, and inspection is performed at Step SA6 by using the newly created inspection recipe (decision threshold value).

Figure 4:
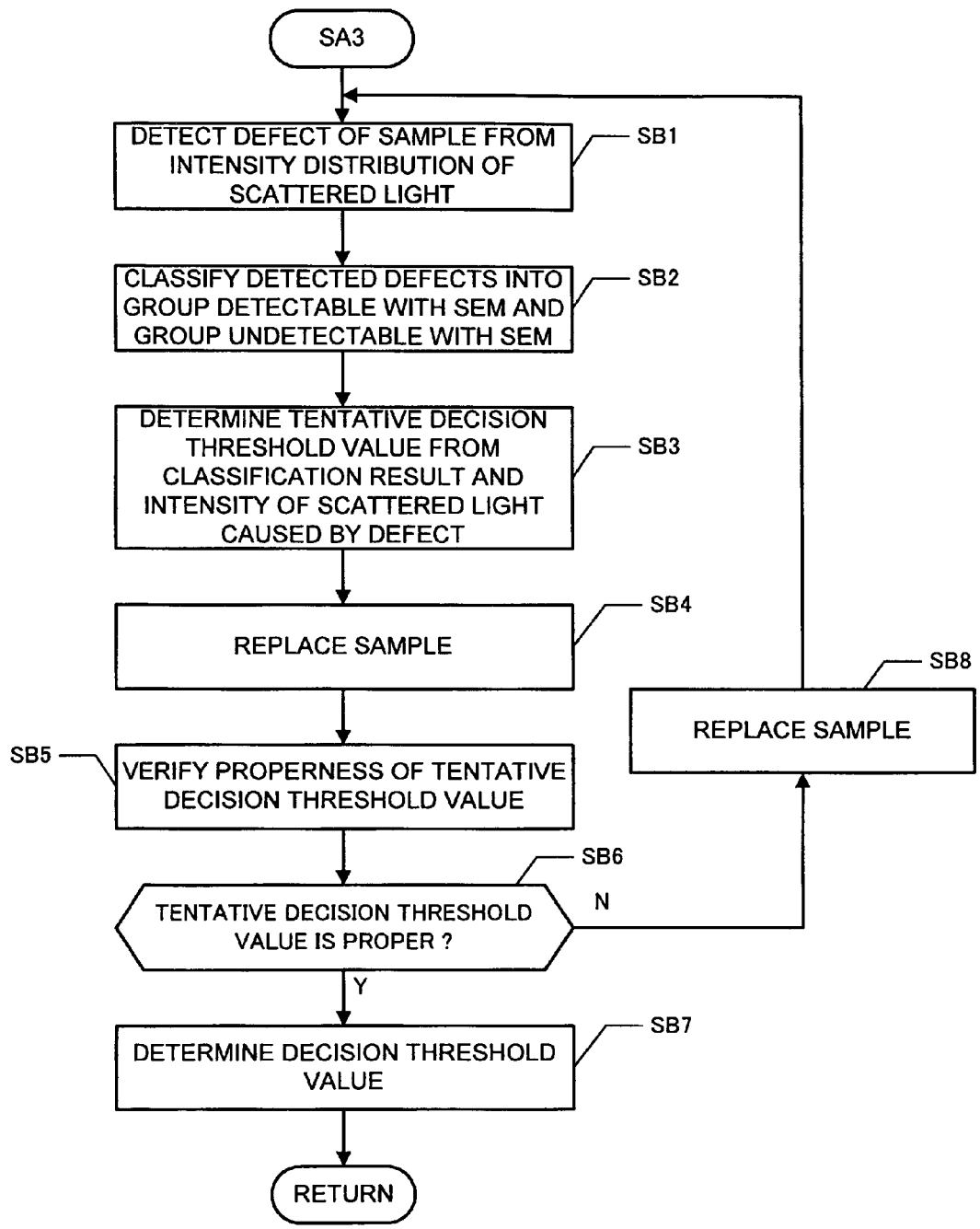
FIG. 4 is a flow chart illustrating a procedure of newly forming inspection recipes of a defect inspection method according to an embodiment.

FIG. 4 is a flow chart showing the details of Step SA3. First, at Step SB1 a sample subjected to the same process as that for the semiconductor wafer to which inspection request was issued, i.e., a sample subjected to the process a for the product type X is held on the stage 2 of the defect inspection apparatus shown in FIG. 1A, and a differential image is measured to detect defects. In this case, for example, one thousand defects in the order of a higher intensity (intensity difference of scattered light) of the differential image are extracted. It is not necessary to fix the number of defects to be extracted to one thousand defects, but the number may be increased or reduced as desired. Serial numbers are given to the defects in the order of a higher intensity difference of scattered light.

Figure 5:
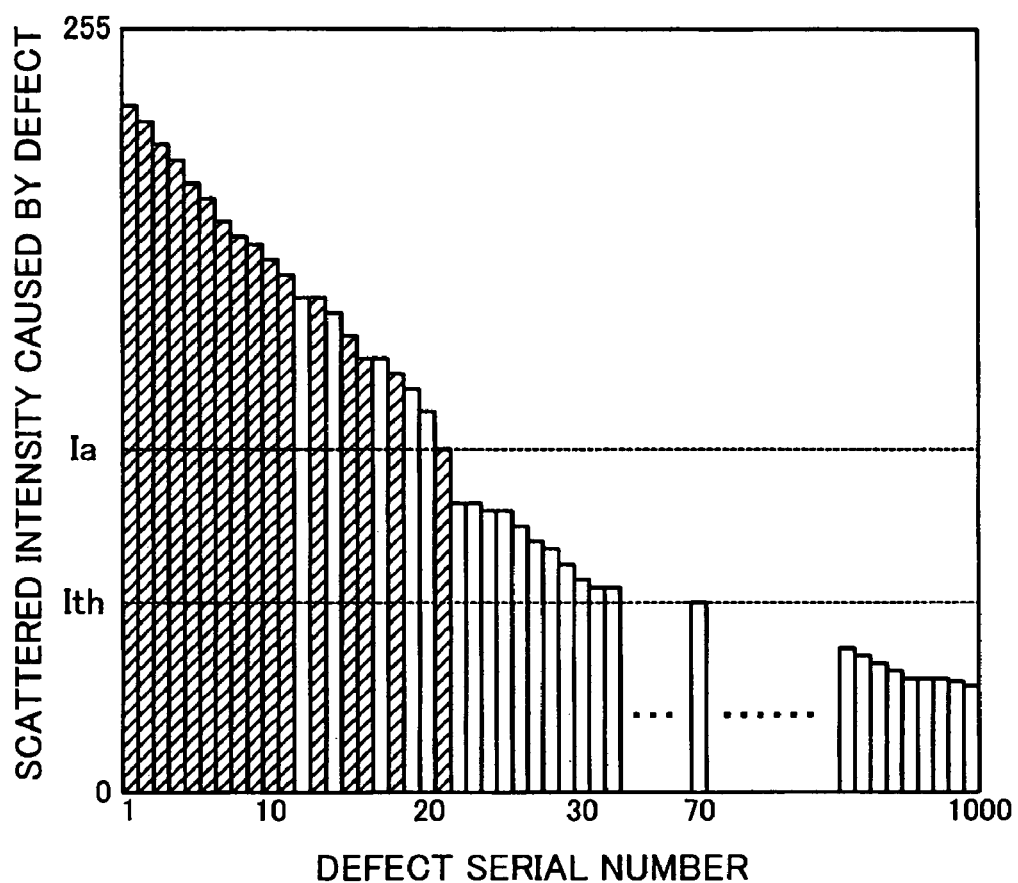
FIG. 5 is a graph showing a relation between a defect and an intensity of scattered light caused by the defect.

FIG. 5 shows a relation between extracted one thousand defects and intensities of scattered light caused by the defects. For example, the intensity of scattered light is represented by 256 steps.

At Step SB2, positions of the extracted one thousand defects are observed with SEM, and the defects are classified into a detectable group and an undetectable group.

With reference to FIGS. 6A to 6F, description will be made on defects detectable with SEM and defects undetectable with SEM.

Figure 6A:
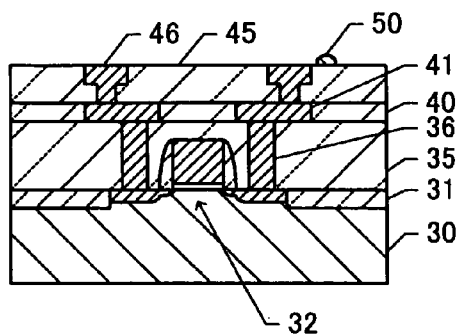
FIGS. 6A and 6D are cross sectional views of semiconductor wafers having foreign matters on a surface layer and in an inner layer.
Figure 6D:
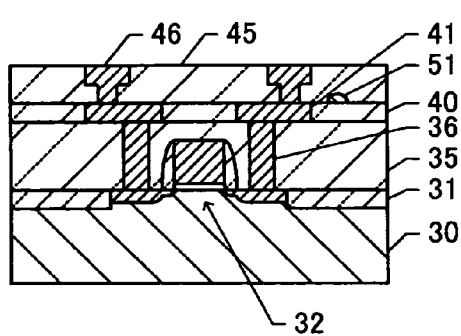

FIGS. 6A and 6D are cross sectional views showing partial regions of semiconductor wafers to be inspected. An isolation insulating film 31 is formed in the surface layer of a silicon substrate 30 to define active regions. A MOSFET 32 is formed in the active region. A first-layer interlayer insulating film 35 is formed on the substrate 30, covering MOSFET 32. A plurality of via holes are formed through the interlayer insulating film 35 and tungsten plugs 36 fill the via holes. Two tungsten plugs 36 are connected to source and drain regions of MOSFET 32, respectively.

A second-layer interlayer insulating film 40 is formed on the interlayer insulating film 35. Copper wirings 41 are formed in the interlayer insulating film 40 by a single damascene method. Another interlayer insulating film 45 is formed on the interlayer insulating film 40. Wirings 46 are formed in the interlayer insulating film 45 by a dual damascene method.

FIG. 6A shows a foreign matter 50 attached to the surface of the uppermost interlayer insulating film 45. FIG. 6D shows a foreign matter 51 attached to the upper surface of the inner interlayer insulating film 40, this foreign matter being covered with the upper interlayer insulating film 45.

Figure 6B:
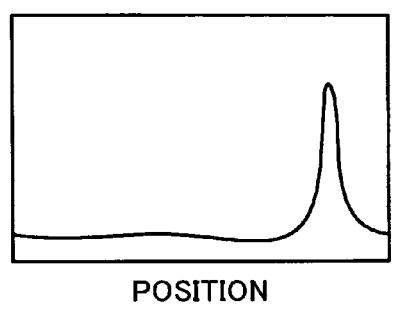
FIGS. 6B and 6E are graphs showing intensity distributions of scattered light caused by the defects (foreign matters) shown in FIGS. 6A and 6D, respectively.
Figure 6E:
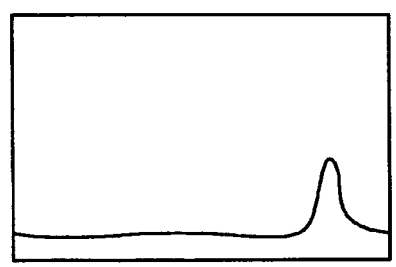

FIGS. 6B and 6E show intensity distributions of scattered light caused by the defects of the semiconductor wafers shown in FIGS. 6A and 6D, respectively. Peaks caused by the foreign matters 50 and 51 shown in FIGS. 6A and 6D respectively appear in the intensity distributions shown in FIGS. 6B and 6E.

Figure 6C:
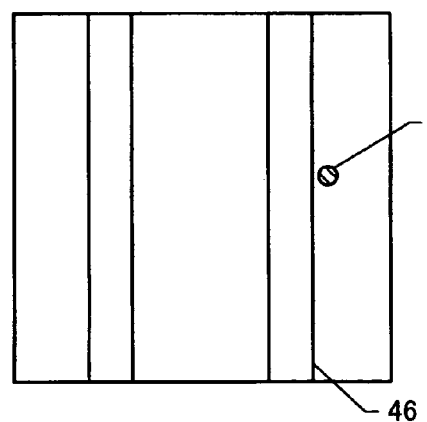
FIGS. 6C and 6F are diagrams sketched from SEM photographs of the semiconductor wafers shown in FIGS. 6A and 6D, respectively.
Figure 6F:
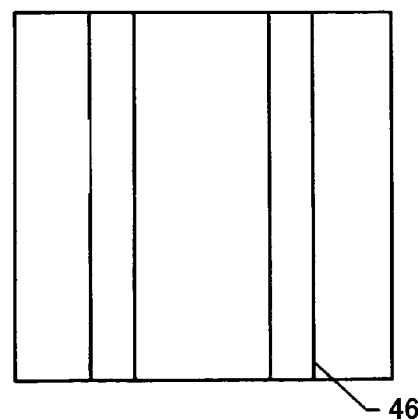

FIGS. 6C and 6F are diagrams sketched from SEM photographs of the semiconductor wafers shown in FIGS. 6A and 6D, respectively. As shown in FIG. 6C, it is possible to observe the foreign matter 50 attached to the exposed surface of the semiconductor wafer. However, as shown in FIG. 6F, the foreign matter 51 located internally cannot be detected with SEM. This foreign matter 51 may be detected with a metallographic microscope. For example, in inspecting the process of forming the wirings 46 by the dual damascene method shown in FIGS. 6A and 6D, the number of foreign matters 50 shown in FIG. 6A attached on the exposed surface is calculated, and it is not necessary to count the number of foreign matters 51 located internally shown in FIG. 6D.

Of the defects shown in FIG. 5, for example, defects detectable with SEM are hatched. Generally, the intensity of scattered light caused by a defect existing on the exposed surface is higher than that caused by a defect located internally. Therefore, defects belonging to the group detectable with SEM are distributed shifted toward the higher intensity of scattered light (toward the smaller serial number affixed to the defect).

For example, in the example shown in FIG. 5, defects having the serial number "11" or smaller can all be detected with SEM. In the serial number range of "12" to "21", defects detectable with SEM and defects undetectable with SEM exist mixedly. All defects having the serial number "22" or larger can not be detected with SEM. Since it can be considered that defects undetectable with SEM exist not on the exposed surface but in the inside of the semiconductor wafer, these defects are not required to be inspected as defects for the process a.

The defect having the lowest scattered light intensity among the defects classified into the group detectable with SEM (defect having the serial number of "21" in the example shown in FIG. 5) is herein called a "a detectable defect having the lowest scatter intensity". It is possible to judge whether the process is normal or not, by counting the number of defects having a scatter intensity equal to or higher than an intensity Ia of scattered light caused by the detectable defect having the lowest scatter intensity. A decision threshold value for the same process as that of a semiconductor wafer having the same product type as that of a sample is preferably set slightly lower than the scattered light intensity Ia, by considering some margin. In the following, the decision threshold value determining method will be described.

Counted is the number of defects having a serial number (defects having the serial numbers "22" to "1000" in the example shown in FIG. 5) larger than the serial number ("21" in the example shown in FIG. 5) of the detectable defect having the lowest scatter intensity. A margin is introduced which is, for example, 5% of the counted number (979 in the example shown in FIG. 5). Specifically, a tentative decision threshold value is set to an intensity Ith of scattered light caused by the defect having a serial number (serial number of "70" in the example shown in FIG. 5) larger by "5%×979"="49" than the serial number of the detectable defect having the lowest scatter intensity.

At Step SB4, another sample of the same product type and the same process is placed on the stage 2 shown in FIG. 1A. At Step SB5 it is verified whether the tentative decision threshold value is proper. Specifically, another tentative decision threshold value of the new sample is calculated by executing the same procedure of Steps SB1 to SB3. The tentative decision threshold value determined for the first sample is compared with the tentative decision threshold value determined for the second sample. If a difference therebetween is in an allowable range, it is judged that the tentative decision threshold value calculated first is proper, whereas if the difference therebetween is not in the allowable range, it is judged that the tentative decision threshold value calculated first is not proper.

If it is judged at Step SB6 that the tentative decision threshold value is proper, this tentative decision threshold value is adopted as a authorized decision threshold value at Step SB7. If it is judged that the tentative decision threshold value is not proper, the sample is replaced with another sample at Step SB8 to return to Step SB1.

The authorized decision threshold value may be determined by evaluating a single sample, or tentative decision threshold values of three or more samples may be calculated to determine a authorized decision threshold value from the calculation results.

Description will be made on the inspection process at Step SA6 shown in FIG. 3. A semiconductor wafer 5 to be inspected is placed on the stage 2. An intensity distribution of scattered light is obtained by scanning the surface of the semiconductor wafer 5 with a laser beam. A difference between scattered light intensity distributions on the surfaces of two chips having congruent patterns is calculated to thereby obtain an intensity distribution (differential image) of scattered light caused by a defect. Defects having the scattered light intensity equal to or larger than the decision threshold value are extracted and counted. If the number of extracted defects is in an allowable range, the process a for the semiconductor wafer 5 is judged normal. If the number of extracted defects is not in an allowable range, the process a for the semiconductor wafer 5 is judged as abnormal. The judgment result is notified to an operator via the I/O device 15.

Next, description will be made on the effects of counting only the defects having a scatter intensity equal to or larger the decision threshold value in the above-described embodiment. Studies are made on a standard sample whose average number of defects on the uppermost layer surface is "10", whose average number of defects in an inner layer is "990", and whose standard deviation σ of total number of defects is "50".

For comparison, studies are made on detecting all defects including in those inner defects without setting a decision threshold value. Generally a process is judged as abnormal if the number of defects is equal to or larger than the average+3σ. Since the average+3σ is "1150", a process is judged as abnormal if the number of detected defects is "1150" or larger.

If a standard product quality is maintained in a process before the process to be inspected, the number of inner defects is nearly "990". Therefore, a process is judged as abnormal if the number of defects on the surface of the uppermost layer is "160" (1150−990=160) or larger, i.e., an average+"150" or larger.

Next, studies are made on counting only the defects having a scatter intensity equal to or higher than the decision threshold value as in the embodiment. It is assumed for example, only six defects were counted among "990" inner layer defects. The remaining "984" defects are not counted up because the intensities of scattered light caused by these defects are equal to or smaller than the decision threshold value. An average number of total defects is "16" (10+4), and the standard deviation σ of counted defects is empirically about "8". In this case, an average+3σ of the number of defects is "40". If a standard product quality is maintained in a process before the process to be inspected, the number of counted inner defects is nearly "6". Therefore, a process is judged as abnormal if the number of defects on the surface of the uppermost layer is "24" or larger, i.e., an average number+"14" or larger.

As described above, if the decision threshold value is not set, a process is judged as abnormal if only the number of defects on the surface of the uppermost layer takes an average value+"150" or larger, whereas if the decision threshold value is introduced as in the embodiment, a process is judged as abnormal if the number of defects on the surface of the uppermost layer takes an average value+"14" or larger. By introducing the decision threshold value, a detection sensitivity of an abnormal process can be increased.

In the embodiment, as indicated at Step SA5 shown in FIG. 3, even if a new product type is added to a manufacture line, the inspection recipe (decision threshold value) associated with a similar process of a conventional product is adopted as the inspection recipe (decision threshold value) for the newly added product type. A work can therefore be omitted which newly creates the inspection recipe each time a new product type is added.

The present invention has been described in connection with the preferred embodiments. The invention is not limited only to the above embodiments. It will be apparent to those skilled in the art that other various modifications, improvements, combinations, and the like can be made.

What we claim are:

1. A defect inspection method comprising steps of:
   (a) observing scattered light from a surface of a sample subjected to a first process;
   (a1) detecting defects from intensities of the scattered light observed at the step (a), and acquiring positions of the detected defects and intensities of the scattered light caused by the detected defects;
   (b0) observing the positions on the surface of the sample acquired at the step (a1) with SEM to determine whether the defects can be detected or cannot be detected at the positions;
   (b) classifying the defects detected at the step (a1) into a SEM detectable group including defects which can be detected at the step (b0) and a SEM undetectable group including defects which cannot be detected at the step (b0); and
   (c) determining a decision threshold value of a scattered light intensity based on the intensity acquired at the step (a) of the scattered light caused by the defect, which the intensity acquired at the step (a1) of the scattered light caused by is lowest among the intensities acquired at the step (a1) of the scattered light caused by the defects classified into the SEM detectable group at the step (b).

2. The defect inspection method according to claim 1, further comprising after the step (c) a step of:
   (d) observing scattered light from a surface of an inspection object subjected to the first process and counting the number of defects presenting a scattered light intensity equal to or larger than the decision threshold value.

3. The defect inspection method according to claim 1, wherein the step (a) observes the scattered light from two areas having congruent patterns formed on the surface of the sample; and
   wherein the step (a1) detects the defects based on a difference between two intensity distributions of the scattered light from the two area.

* * * * *